(12) United States Patent
Dolan

(10) Patent No.: US 6,398,093 B1
(45) Date of Patent: Jun. 4, 2002

(54) CUTTING DEVICE FOR DENTAL FLOSS

(75) Inventor: John Dolan, Boothwyn, PA (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 09/293,123

(22) Filed: Apr. 16, 1999

(51) Int. Cl.$^7$ .............................. B26F 3/02; B65H 35/10
(52) U.S. Cl. ............................ 225/51; 225/63; 225/64; 225/82; 225/84; 225/85; 225/91; 225/41; 242/138
(58) Field of Search .................. 225/51, 52, 63, 225/64, 82, 83, 84, 85, 91, 41, 47, 46, 48; 242/138

(56) References Cited

U.S. PATENT DOCUMENTS

| | | | |
|---|---|---|---|
| 752,845 A | 2/1904 | Laird | |
| 889,429 A | 6/1908 | Benda | |
| 1,220,760 A | 3/1917 | LeClerc | |
| 1,229,504 A | 6/1917 | Olson | |
| 1,926,539 A | 9/1933 | Hurst | |
| 2,145,178 A | 1/1939 | Hawkins | |
| 2,302,965 A | 11/1942 | Lucia | |
| 3,746,225 A | * 7/1973 | Runckel | 225/45 X |
| 4,050,648 A | 9/1977 | Tisma | 242/129.8 |
| 4,073,419 A | * 2/1978 | Tarrson et al. | 225/46 X |
| 4,141,519 A | * 2/1979 | Tarrson et al. | 242/138 X |
| 4,925,073 A | * 5/1990 | Tarrson et al. | 225/46 X |
| 5,156,311 A | * 10/1992 | Spencer, Jr. et al. | 225/41 |
| 5,199,622 A | 4/1993 | Vieau | 225/51 |
| 5,282,563 A | * 2/1994 | Oliver et al. | 225/47 |
| 5,518,012 A | 5/1996 | Dolan et al. | 132/321 |
| 5,649,659 A | * 7/1997 | Saunders | 225/39 |
| 5,806,666 A | * 9/1998 | Chiang et al. | 225/47 X |

* cited by examiner

*Primary Examiner*—M. Rachuba

(57) ABSTRACT

A device for severing and restraining dental floss that has a blade with a restraining side and a cutting side, which can be formed by slanting the blade or otherwise providing a narrow pinching portion on one side of the blade to restrain the floss.

5 Claims, 3 Drawing Sheets

CUTTING DEVICE FOR DENTAL FLOSS

BACKGROUND OF THE INVENTION

1. Field of Invention

The present invention relates to a cutting or severing apparatus or device for separating a quantity of floss material from its supply reservoir, and particularly to an apparatus or device for severing floss material made from expanded polytetrafluoroethylene (PTFE) fibers while also restraining the dental floss material in a manner that prevents the floss material from returning to its reservoir after severance.

2. Description of Related Art

Presently, there are a number of commercially available severing devices which are designed to sever dental floss and as well as to retain the unused portion of dispensed floss. An example is U.S. Pat. No. 4,050,648 to Tisma which teaches a floss dispenser system that maintains friction on the supply spool while the floss is dispensed. This prevents the unused floss from returning back to the floss supply spool after a section has been severed by a blade affixed to the dispenser. U.S. Pat. No. 5,199,622 to Vieau teaches a cantilever blade type cutter which has a depression or cutout element extending from the blade. The depression restrains the floss under the blade while the floss is cut by the perimeter. The entire perimeter of the blade is the cutting device. Unfortunately, with blade devices such as the one taught by Vieau, the floss material passes under the blade past the depression while the floss is dispensed. This may scrape away any coating, such as natural beeswax or medicament, which is deposited on the surface of the floss material. This unfortunate condition is further exacerbated when dispensing floss material made of expanded polytetrafluoroethylene (PTFE) such as taught in U.S. Pat. No. 5,518,012 to Dolan et al. The compressive nature of expanded PTFE permits the floss material to compress under the blade device into a denser filament, thus rendering the filament less effective to remove debris in the oral cavity during flossing.

A floss cutting device which does not compress the floss material prior to severing, does not remove coatings deposited on the floss material, restrains the severed end of undispensed floss, and provides a superior cutting device, would be desirable.

SUMMARY OF THE INVENTION

The present invention provides an improved cutting device for dental floss, and especially for highly compressible floss material such as floss material made of expanded polytetrafluoroethylene (PTFE), as well as coated, impregnated floss materials. The present invention also provides a cutting device with the added benefit of restraining the undispensed, severed end of dental floss using a novel technique not previously found in the art. The cutting device of present invention is mounted on a floss dispensing container in a location such that the user is able to easily position floss material dispensed from the supply spool under the blade and sever the floss.

The invention provides a device for severing and restraining a filament comprising a base having a restraining portion and a blade extending from the base, the blade having a first edge juxtaposed to the restraining portion of base to form a pinching element adapted to restrain the filament between the first edge and the restraining portion and a second edge adapted to sever the filament.

Also provided is a dental floss dispenser comprising a housing, a spool of dental floss disposed within the housing, and a device for severing and restraining the dental floss mounted on the housing, the device comprising a base having a restraining portion and a blade extending from the base, the blade having a first edge juxtaposed to the restraining portion of the base to form a pinching element adapted to restrain the filament between the first edge and the restraining portion and a second edge adapted to sever the filament.

The present invention is also suitable for use in severing fishing line, sewing thread, counted cross stitch floss, and other filaments which may be housed in a dispensing reservoir.

DESCRIPTION OF THE DRAWINGS

The operation of the present invention should become apparent from the following description when considered in conjunction with the accompanying drawings, in which.

DETAILED DESCRIPTION OF THE INVENTION

The present invention is an improved cutting blade for use as a cutting device for dental floss and especially for highly compressible floss. As the term "floss" is used herein, it is intended to encompass a thread-like member used for disturbing and removing plaque and other material from the oral cavity.

The cutting device of the present invention comprises a blade and a base. The base is the foundation of the blade. Both the base and the blade may be formed using convention metal forming techniques such as stamping, coining, bending, punching, and shearing, etc. The base is of such configuration that it may be easily mounted on a floss dispenser.

Figure 1:
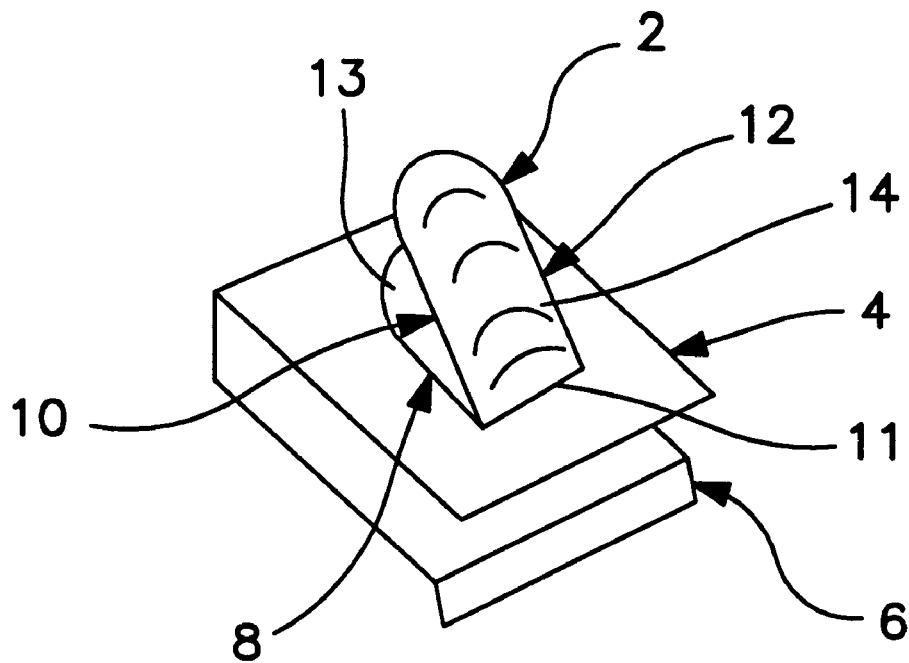
FIG. 1 is an isometric view from the front-top perspective of a cutting device according to an exemplary embodiment of the present invention.
Figure 3:
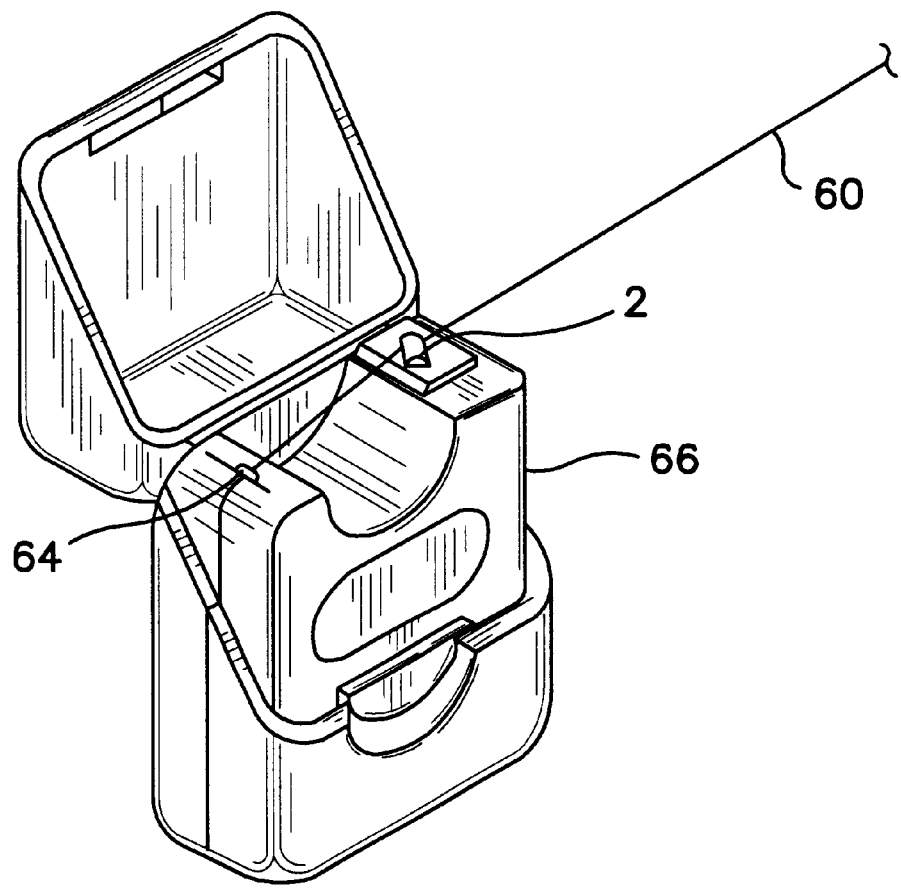
FIG. 3 is a three-quarter isometric view of the exemplary cutting device of FIG. 1 mounted on a floss dispenser.

FIG. 1 illustrates an exemplary embodiment of the present invention. In the embodiment of FIG. 1, a cantilever blade 2 extends from a base 4. A lip 6 is formed as part of base 4 to facilitate placing the device on a floss dispenser 66 as shown in FIG. 3. Still referring to FIG. 3, a dental floss strand 60 exits the dispenser 66 from a hole 64 in the dispenser 66. After a user pulls a desired quantity from dispenser 66, the user places strand 60 under blade 2.

Referring back to FIG. 1, blade 2 has a restraining side 10 and a cutting side 12. Base 4 has a corresponding restraining portion 8 which, in the exemplary embodiment shown, is the side of a hole 13 formed under blade 2 when blade 2 is formed from base 4. Restraining portion 8 and restraining side 10 together form a pinching element. Restraining side 10 of blade 2 is configured so as aggressively to hold a floss strand under blade 2 by pinching the floss strand between restraining side 10 and restraining portion 8 of base 4. In order to accomplish this restraining function, blade 2 may be slanted such that a point on restraining side 10 is closer to base 4 than a corresponding point on cutting side 12. That is, a point a fixed distance from a crease 11 along restraining side 10 is closer to base 4 in a distance measured vertically from restraining portion 8 (this distance is designated A in FIG. 2C) than a corresponding point an equivalent distance up cutting side 12 from crease 11 of blade 2 (this distance is designated B in FIG. 2C). As an alternative to so slanting blade 2, restraining side 10 may simply have a dimple or other additional material extending from it to create the desired pinch point.

As a floss strand is forced under restraining side 10 of blade 2, it is pinched between restraining side 10 and restraining portion 8. The floss strand may then be severed by slicing it along cutting side 12 of blade 2. The cutting is facilitated because the floss is held taut between restraining side 10 and a user's grasp of the floss strand. As the floss is dispensed from a spool (not shown) within dispenser 66 (FIG. 3) through hole 64, it should not be pulled under blade 2. If it is, because of the proximity of restraining side 10 to restraining portion 8, the floss will be severed immediately. Accordingly, a user will remove a floss strand from under blade 2 to dispense the floss, then insert the floss strand under the blade for cutting as described above. This prevents dragging the floss under the blade with the consequent removal of any coating on the floss strand. This is particularly beneficial because the floss will retain the full benefits of having any coating on it when used by the user. The coating and any materials contained within it are not rubbed off by the blade.

Figure 2A:
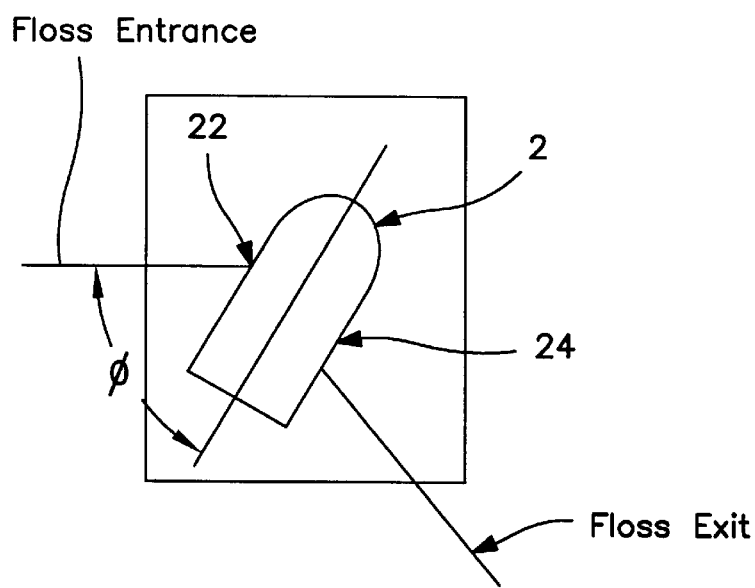
FIG. 2A is a top view of the exemplary cutting device shown in FIG. 1.
Figure 2B:
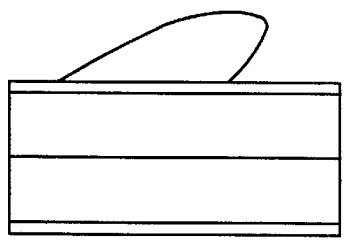
FIG. 2B is a front view of the exemplary cutting device shown in FIG. 1.
Figure 2C:
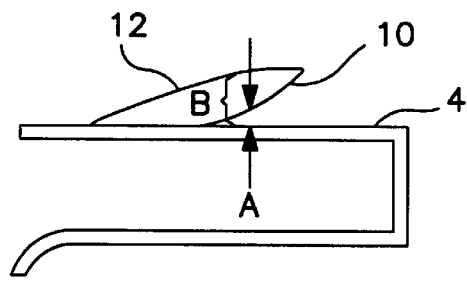
FIG. 2C is a side view of the exemplary cutting device shown in FIG. 1.

Further description of how the floss is actually severed will now be provided. As shown in FIG. 2, blade 2 may be oriented to create an angle φ which is less than π/2 radians such that the floss entering the blade at point 22 is then deflected by a user down towards point 24 where it exits from under blade 2. The arch or deflection of the floss under blade 2 is induced by the user but results from the exit point 24 being below the floss entering under blade 2 at point 22. This deflection helps to create an improved gripping or pinching action of the floss at point 22. Additionally, as the floss is restrained at point 22, a moment is thus induced around point 22 as the floss direction or angle of movement along its length now deviates from its direction created by the floss being originally suspended between floss exit hole 64 and point 22, and now is in the direction between point 22 and point 24. A sliding action along edge 14 severs the floss. This mode of severing is referred to as shearing, as opposed to ripping. Shearing is believed to be the preferred mode for severing floss materials made of expanded polytetrafluoroethylene.

As described above, when the floss is restrained between restraining side 10 and restraining portion 8, it provides a pinch point to allow easy severance of the floss strand. In addition, this pinch point also allows the floss strand to be restrained after severance from returning back into dispenser 66.

Using the present invention, a floss strand may be reliably and easily severed from a dispensing spool while the severed end is restrained from returning to the spool. This is accomplished using a blade that has a restraining side and a cutting side, which can be formed by slanting the blade or otherwise providing a narrow pinching portion on one side of the blade to restrain the floss.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A device for severing and restraining a filament comprising a base having a restraining portion and a blade extending from said base, said blade having a first edge adjacent to said restraining portion of said base to form a pinching element adapted to restrain said filament between said first edge and said restraining portion and a second edge adapted to sever said filament.

2. A device for severing and restraining a filament as defined in claim 1 wherein said filament is dental floss.

3. A device for severing and restraining a filament as defined in claim 2 wherein said dental floss is expanded PTFE fiber.

4. A device for severing and restraining a filament as defined in claim 1 wherein said blade is slanted such that said first edge is closer to said base than said second edge.

5. A dental floss dispenser comprising a housing, a spool of dental floss disposed within said housing, and a device for severing and restraining said dental floss mounted on said housing, said device comprising a base having a restraining portion and a blade extending from said base, said blade having a first edge adjacent to said restraining portion of said base to form a pinching element adapted to restrain said filament between said first edge and said restraining portion and a second edge adapted to sever said filament.

* * * * *